US011253367B2

(12) United States Patent
Lee et al.

(10) Patent No.: US 11,253,367 B2
(45) Date of Patent: Feb. 22, 2022

(54) SCAFFOLD FOR BONE REGENERATION

(71) Applicant: Institute for Advanced Engineering, Yongin-si (KR)

(72) Inventors: Kyoung-Don Lee, Yongin-si (KR); Tae-Suk Suh, Yongin-si (KR); Jong Won Rhie, Yongin-si (KR); Ki-Young Park, Yongin-si (KR); Jae-Sung Kim, Yongin-si (KR); Byeong-Ju Jin, Yongin-si (KR); Ki Joo Kim, Yongin-si (KR); Do-kun Yoon, Yongin-si (KR)

(73) Assignee: Institute for Advanced Engineering, Yongin-si (KR)

( * ) Notice: Subject to any disclaimer, the term of this patent is extended or adjusted under 35 U.S.C. 154(b) by 158 days.

(21) Appl. No.: 16/564,653

(22) Filed: Sep. 9, 2019

(65) Prior Publication Data

US 2020/0163772 A1    May 28, 2020

(30) Foreign Application Priority Data

Nov. 28, 2018    (KR) .......................... 10-2018-0150158

(51) Int. Cl.
*A61F 2/28*    (2006.01)
*A61F 2/30*    (2006.01)

(52) U.S. Cl.
CPC ...... *A61F 2/2846* (2013.01); *A61F 2002/285* (2013.01); *A61F 2002/30433* (2013.01)

(58) Field of Classification Search
CPC .................................. A61F 2/28; A61B 17/80
See application file for complete search history.

(56) References Cited

U.S. PATENT DOCUMENTS

2004/0102776 A1 *    5/2004    Huebner ............ A61B 17/8052
                                                    606/281
2019/0209327 A1 *    7/2019    Fitzpatrick ............... A61F 2/28

FOREIGN PATENT DOCUMENTS

KR    10-2018-0079297 A    7/2018
WO    2017-042366 A1        3/2017

OTHER PUBLICATIONS

Office Action dated Dec. 17, 2018, in corresponding Korean Application No. 10-2018-0150158, with machine translation; 11 pages.

* cited by examiner

*Primary Examiner* — Yashita Sharma
(74) *Attorney, Agent, or Firm* — Maier & Maier, PLLC

(57) ABSTRACT

There is provided a scaffold for bone regeneration which is adapted to be implanted at a bone defect site of a bone. The scaffold comprises a main support member configured to be fixed to the bone, and a load supporting unit configured to be installed in the bone defect site of the bone to selectively bear a load applied to the bone. The load supporting unit includes one or two supporting pieces to be installed in the bone defect site of the bone to selectively bear a load applied to the bone. The supporting piece has at one end portion a contact portion to be brought into contact with and fixed to a compact bone in the bone defect site of the bone. The other end portion of the supporting piece is selectively coupled to the main support member.

9 Claims, 10 Drawing Sheets

SCAFFOLD FOR BONE REGENERATION

CROSS-REFERENCE TO RELATED APPLICATION

This application claims priority to Korean Patent Application No. 10-2018-0150158, filed on Nov. 28, 2018, the entire contents of which are incorporated herein by reference.

FIELD OF THE INVENTION

The present disclosure relates to a scaffold for bone regeneration.

BACKGROUND OF THE INVENTION

A scaffold for bone regeneration refers to a member that is implanted in a human body in the field of dentistry or orthopedics to replace a bone of the human body damaged by disease or accident. The scaffold is implanted in a bone defect site to complement the bone defect, and there are largely two methods for scaffold implantation. One is the implantation of a patient's own bone to the affected part, and the other one is the implantation of an artificial scaffold.

In the method of implanting the patient's own bone, another bone defect occurs by extracting a bone to be implanted, and there is a risk of causing an unexpected sequel. Therefore, the method of implanting an artificial scaffold in a bone defect site is generally used.

In a conventional method of implanting an artificial scaffold, the scaffold is mainly formed of a material such as titanium, ceramics or the like.

Meanwhile, studies have been made to use a scaffold formed of a bioactive material in a bone defect site. The bioactive scaffold is used to be implanted in the bone defect site for the purpose of regenerating bone tissues after a certain period of time to recover its original function in cooperation with the existing bones. At this time, the bioactive scaffold needs to have sufficient rigidity before the bone is completely regenerated in the bone defect site, and proper loads need to be repeatedly acted on the regenerated bone so that the completely regenerated bone itself has sufficient rigidity. That is, in order for the bioactive scaffold to have rigidity substantially equal to that of the existing bone, the regenerated bone tissues need to receive a load over a certain period of time.

However, it is difficult to remove the conventional scaffold after it is implanted in a bone defect site, and it is difficult for the regenerated bone to have rigidity since the scaffold for bone regeneration bears the load instead of the growing bone.

Accordingly, a technique of allowing the rigidity of the scaffold to be maintained during the bone regeneration and allowing a load to be applied to the regenerated bone while preventing any load from being applied to the remaining scaffold after the regenerated bone becomes to have a certain level of rigidity.

SUMMARY OF THE INVENTION

In view of the above, the present disclosure provides a scaffold for bone regeneration capable of allowing the rigidity of the scaffold to be maintained during the bone regeneration and allowing a load to be applied to the regenerated bone while preventing any load from being applied to the remaining scaffold after the regenerated bone becomes to have sufficient rigidity.

In accordance with an aspect of the present disclosure, there is provided a scaffold for bone regeneration to be implanted at a bone defect site of a bone, the scaffold comprising: a main support member to be fixed to the bone; and a load supporting unit to be installed in the bone defect site of the bone to bear a load applied to the bone, wherein the load supporting unit includes a supporting piece having a shape bent in two or more steps, the supporting piece having a contact portion to be brought into contact with and fixed to a compact bone in the bone defect site of the bone.

The supporting piece may comprise a contact portion serving to bear a load applied to the compact bone; a compact bone support portion bent to extend from the contact portion, the compact bone support portion serving to bear a load applied to the compact bone; a spongy bone support portion bent to extend from the compact bone support portion, the spongy bone support portion adapted to be disposed in a region overlapping a spongy bone of the bone in an extending direction of the bone; and a load transfer interruption portion bent to extend from the spongy bone support portion.

The supporting piece may comprise two supporting pieces, and the supporting pieces may be connected to each other by a fixing member inserted through fastening holes formed in the load transfer interruption portions of the supporting pieces.

The main support member may include a connecting hole formed therein, and the fixing member is inserted through the connecting hole and the fastening holes to fix the load transfer interruption portions to the main support member.

The contact portion may comprise a plurality of contact portions, and the compact bone support portion may have the same number of branches as the number of the contact portions.

The main support member may have an auxiliary hole formed therein, the supporting piece may further comprise a protruding portion protruding from the compact bone support portion, and the main support member and the load supporting unit may be coupled to each other by a fixing member inserted through the auxiliary hole into a recess of the protruding portion.

In accordance with another aspect of the present disclosure, there is provided a scaffold for bone regeneration to be implanted at a bone defect site of a bone, the scaffold comprising: a main support member to be fixed to the bone; and a load supporting unit to be installed in the bone defect site of the bone to selectively bear a load applied to the bone.

The load supporting unit may include two supporting pieces to be installed in the bone defect site of the bone to selectively bear the load applied to the bone, and the supporting pieces may have at one end portions contact portions to be brought into contact with and fixed to opposite faces of a compact bone in the bone defect site of the bone, respectively, the other end portions of the supporting pieces being selectively coupled to or decoupled from each other.

Each of the supporting pieces may comprise a first support portion extending from the contact portion in a direction away from corresponding one of the opposite faces of the compact bone, the first support portion serving to bear a load applied to the compact bone; a second support portion extending from the first support portion in a direction toward the main support member, the second support portion adapted to be disposed in a region overlapping a spongy bone in the bone defect site of the bone in an extending direction of the bone; and a third support portion extending from the second support portion in a direction away from the corresponding one of the opposite faces of the compact bone, wherein the supporting pieces are coupled to each other and fixed to the main support member by a fixing member inserted through a connecting hole formed in the main support member into fastening holes formed in the third support portions, and wherein the supporting pieces are decoupled from each other by removing the fixing member to interrupt a transfer of a load through the supporting pieces.

The main support member may have an auxiliary hole formed therein, each of the supporting pieces may further comprise a protruding portion protruding from the first support portion, and the main support member and the load supporting unit may be coupled to each other by a fixing member inserted through the auxiliary hole into a recess of the protruding portion.

According to the aspect of the present disclosure, the stiffness of the scaffold is maintained during bone regeneration, and when the regenerated bone has a sufficient stiffness after a certain period of time, a load is applied to the regenerated bone even if the implanted scaffold is still remained.

BRIEF DESCRIPTION OF THE DRAWINGS

The objects and features of the present disclosure will become apparent from the following description of embodiments, given in conjunction with the accompanying drawings, in which.

DETAILED DESCRIPTION OF THE EMBODIMENTS

Figure 1:
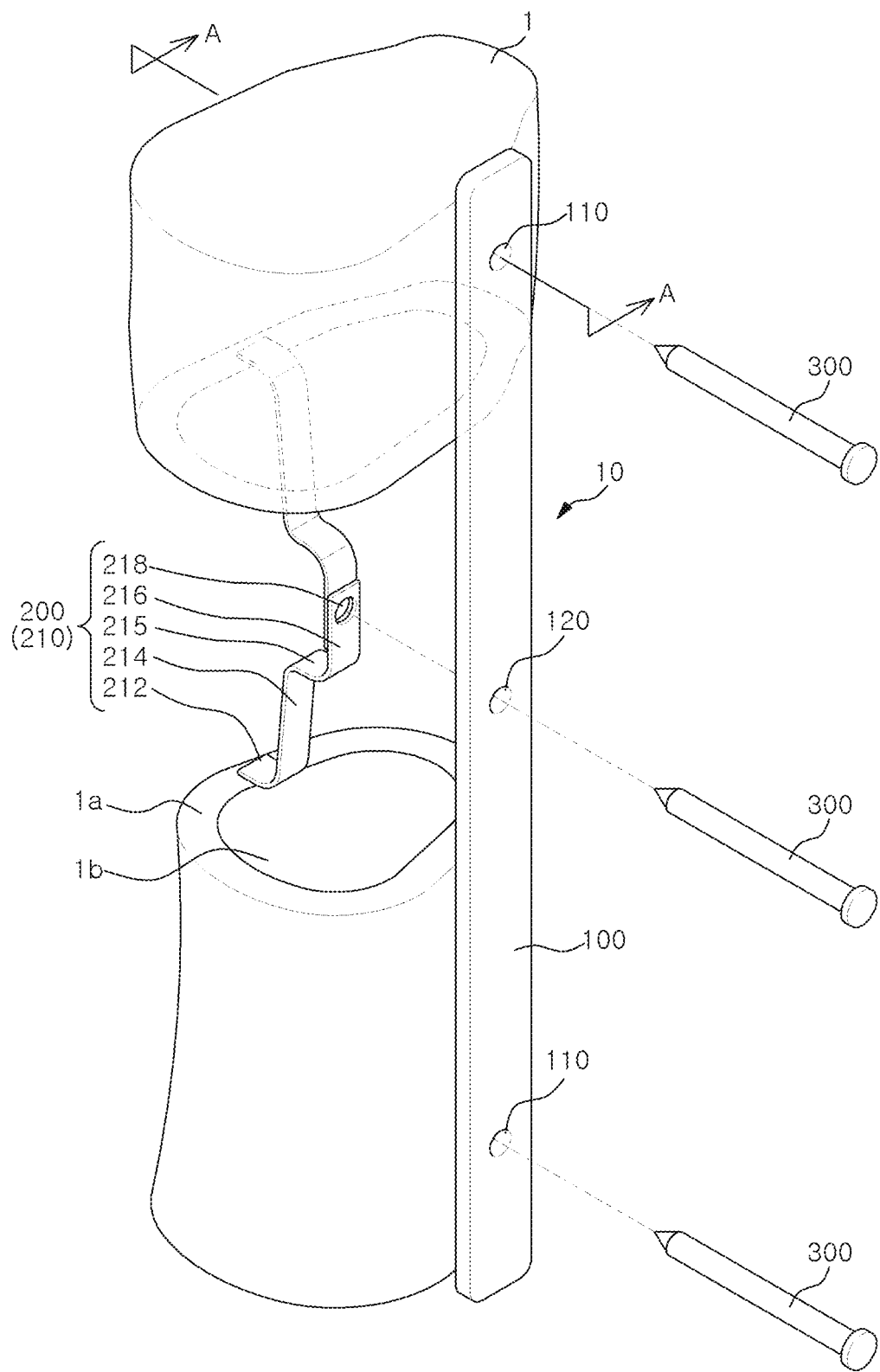
FIG. 1 is a view showing a scaffold for bone regeneration according to an embodiment of the present disclosure.

Hereinafter, configurations and operations of embodiments will be described in detail with reference to the accompanying drawings. The following description is one of various patentable aspects of the disclosure and may form a part of the detailed description of the disclosure.

In describing the embodiments of the present disclosure, the detailed descriptions of well-known functions or configurations will be omitted if it is determined that the detailed descriptions of well-known functions or configurations may unnecessarily make obscure the spirit of the present disclosure.

The disclosure may be variously modified and may include various embodiments. Specific embodiments will be exemplarily illustrated in the drawings and described in the detailed description of the embodiments. However, it should be understood that they are not intended to limit the disclosure to specific embodiments but rather to cover all modifications, similarities, and alternatives which are included in the spirit and scope of the disclosure.

The terms used herein, including ordinal numbers such as "first" and "second" may be used to describe, and not to limit, various components. The terms simply distinguish the components from one another.

When it is said that a component is "coupled" or "linked" to another component, it should be understood that the former component may be directly connected or linked to the latter component or a third component may be interposed between the two components.

Specific terms used in the present application are used simply to describe specific embodiments without limiting the disclosure. An expression used in the singular encompasses the expression of the plural, unless it has a clearly different meaning in the context.

Hereinafter, embodiments of the present disclosure will be described in detail with reference to the accompanying drawings.

A scaffold for bone regeneration according to the embodiments of the present disclosure is adapted to be implanted at a bone defect site of a patient suffering from a bone defect due to factors such as fracture accident or surgery. The scaffold for bone regeneration serves to assist bone reconstruction in the bone defect side while compensating for the bone defect.

In addition, the system and method for manufacturing a scaffold for bone regeneration according to the embodiments of the present disclosure are provided to manufacture a scaffold for bone regeneration capable of bear a variety of loads such as compression, tensile, shearing, bending, buckling and the like resulting from bone-deficient physical characteristics of a patient and patient's activities in daily life after recovery.

To this end, the system and method for manufacturing a scaffold for bone regeneration according to embodiments of the present disclosure can define key mechanical structural strength variable and design a specific shape and material of a scaffold for bone regeneration to have similar structural strength within an error range depending on physical properties of a bone defect site of a patient to manufacture a patient-customized scaffold based thereon.

The scaffold thus manufactured may have various shapes, and the shape of the scaffold may be determined depending on the implantation region, the defect amount of the bone defect site, the shape of the bone defect site, and the like.

Hereinafter, various embodiments of the scaffold thus manufactured will be described, and then a specific system and method for manufacturing the same will be described.

FIGS. 1 to 5 show various shapes of the scaffold produced by the manufacturing method according to the present disclosure. Although the scaffold shown in each drawing has a shape having a predetermined thickness derived from the design result, the scaffold is represented by a solid line while omitting the thickness for the sake of simplicity. The shapes of the scaffold shown in FIGS. 1 to 5 are examples of shapes designed and manufactured by the manufacturing method according to the present disclosure. The shape of the scaffold may be designed and manufactured differently based on various factors such as the patient's condition, bone defect pattern, physician's requirements and the like.

Figure 2:
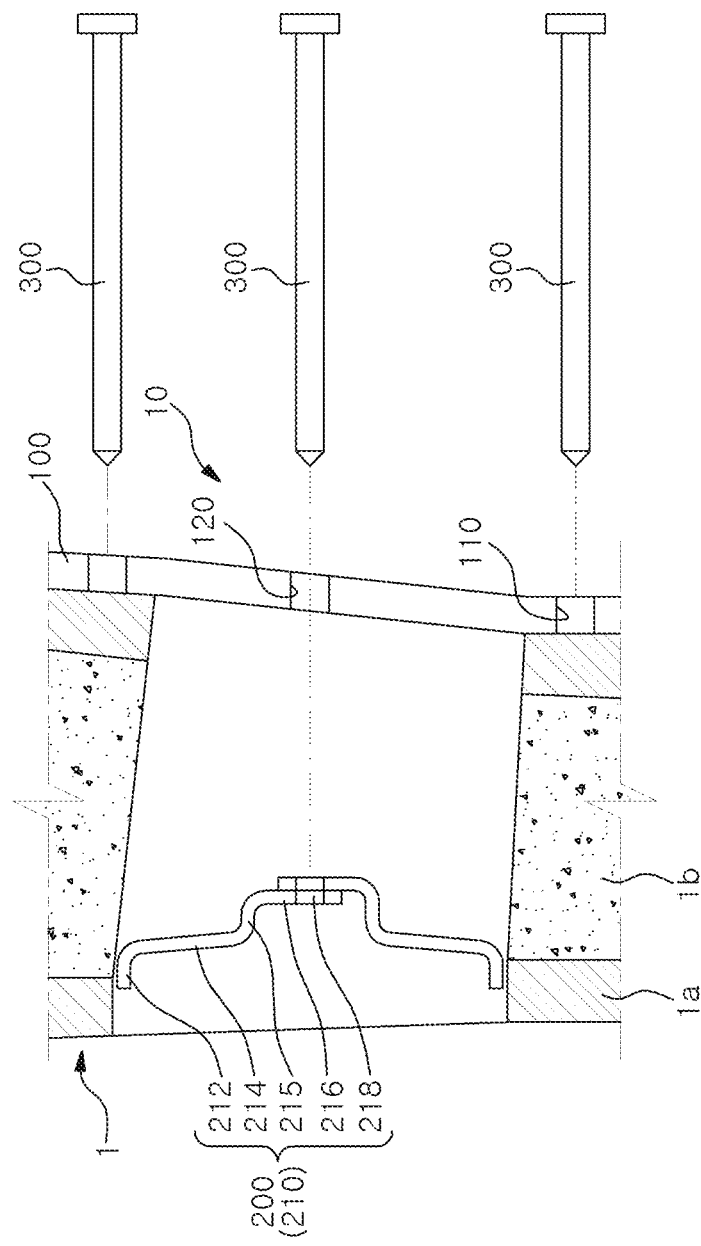
FIG. 2 is a cross-sectional view taken along line A-A in FIG. 1.

Referring to FIGS. 1 and 2, a scaffold for bone regeneration 10 (hereinafter, also referred to simply as "scaffold") according to an embodiment of the present disclosure includes a main support member 100 and a load supporting unit 200. The main support member 100 is made of a material such as metal or ceramics and is fixed to the surface of a bone 1 including a defect site to bear loads acting on the bone 1 and protect the bone 1 during the growth of the tissues of the bone 1.

The main support member 100 is provided in a plate shape, for example, and includes a fixing hole 110 and a connecting hole 120 formed at a portion corresponding to the bone defect site.

A fixing member 300 is inserted through the fixing hole 110 and is fixed to the bone 1, thereby fixing the main support member 100 to the bone 1. The fixing member 300 may be a pin, a screw or the like.

The load supporting unit 200 can be fixed to the main support member 100 by inserting a fixing member 300 through the connecting hole 120 of the main support member 100 into a fastening hole 218 of the load supporting unit 200 to be described later.

The load supporting unit 200 is installed in the bone defect site of the bone 1 to selectively bear a load applied to the bone 1. The load supporting unit 200 includes a supporting piece 210 having a shape bent in two or more steps.

The load supporting unit 200 may include one or more supporting pieces 210. For example, two supporting pieces 210 are provided as shown in FIGS. 1 to 5, and the supporting pieces 210 are fixed to each other by the fixing member 300 inserted into the fastening holes 218.

The shape of the supporting piece 210, such as the sectional area and thickness of the supporting piece 210, may be selected in consideration of the ratio of the rigidity of the material of the supporting piece 210 to the rigidity of a compact bone 1a of the bone 1.

Parameters, such as the centroid of the scaffold 10, the moment of inertia with respect to the centroid, and the principal axes of the moment of inertia, are selected to be the same as those before the damage of the bone 1 depending on the outer shape of the bone defect site and the thickness of the compact bone 1a.

The supporting piece 210 includes a contact portion 212, a compact bone support portion 214, a spongy bone support portion 215, and a load transfer interruption portion 216. For example, the supporting piece 210 may be manufactured through a 3D printing technique, but the present disclosure is not limited thereto. The compact bone support portion 214, the spongy bone support portion 215 and the load transfer interruption portion 216 in the present embodiment correspond to a first support portion, a second support portion and a third support portion described in the claims.

The contact portions 212 of the supporting members 210 are adapted to be brought in contact with and fixed to opposite faces of the compact bone 1a in the bone defect site of the bone 1. At this time, the contact portions 212 may be adhered to the opposite faces or the side surface of the compact bone 1a using a harmless adhesive or a mechanical fastener such as a screw, and the contact portions 212 may be attached to the opposite faces of the compact bone 1a merely by restoring force of the supporting pieces 210. The opposite faces of the compact bone 1a in the bone defect site of the bone 1 mean the facing surfaces of the compact bones 1a with the bone defect site of the bone 1 therebetween as shown in FIG. 2. The positions of the upper and the lower contact portion 212 may be different in a direction perpendicular to the extending direction of the bone 1.

The compact bone support portion 214 is bent to extend from the contact portion 212 and serves to bear a load applied to the compact bone 1a. For example, the compact bone support portion 214 may extend from the contact portion in a direction away from corresponding one of the opposite faces of the compact bone 1a.

The spongy bone support member 215 is bent to extend from the compact bone support member 214 and is adapted to be disposed in a region overlapping the spongy bone 1b of the bone 1 in the bone extending direction. In other words, the spongy bone support member 215 may be disposed in a space defined between the opposite faces of the spongy bone 1b in the bone defect site of the bone 1. When the spongy bone support member 215 is projected in the extending direction of the bone 1, the projected spongy bone support member 215 may be disposed in the region of the spongy bone 1b in the bone defect site of the bone 1. For example, the spongy bone support member 215 may extend from the compact bone support portion 214 in a direction toward the main support member 100. Therefore, a load applied to the areas of the compact bone 1a and the spongy bone 1b can be received by the compact bone support portion 214 and the spongy bone support portion 215 until the sufficiently grown regenerated tissues are filled in the bone defect site.

In addition, the load transfer interruption portion 216 is bent to extend from the spongy bone support portion 215, and a fastening hole 218 is formed in the load transfer interruption portion 216. For example, the load transfer interruption portion 216 may extend from the contact portion in a direction away from the corresponding one of the opposite faces of the compact bone 1a.

The supporting pieces 210 are fixed to each other by inserting the fixing member 300 into the fastening holes 218 formed in the respective supporting pieces 210.

The main support member 100, the supporting pieces 210 and the fixing member 300 are configured such that the fixing member 300 inserted through the connecting hole 120 and the fastening holes 218 does not overlap the compact bone 1a in the extending direction of the bone 1. Therefore, when the compact bone 1a is regenerated in the bone defect site, the fixing member 300 does not interfere with the regenerated compact bone 1a.

Accordingly, the fixing member 300 is inserted in the fastening holes 218 of the supporting pieces 210 so that the supporting pieces 210 bear the load applied to the bone 1 before the bone 1 is sufficiently regenerated in the bone defect site. When the bone is sufficiently regenerated, the fixing member 300 can be removed so that the regenerated bone bears the load applied to the bone 1, which allows the rigidity of the bone 1 to be recovered as before. The fixing member 300 is configured to be removed from the supporting members 210 and the main support member 100 when the bone is sufficiently regenerated.

Figure 3:
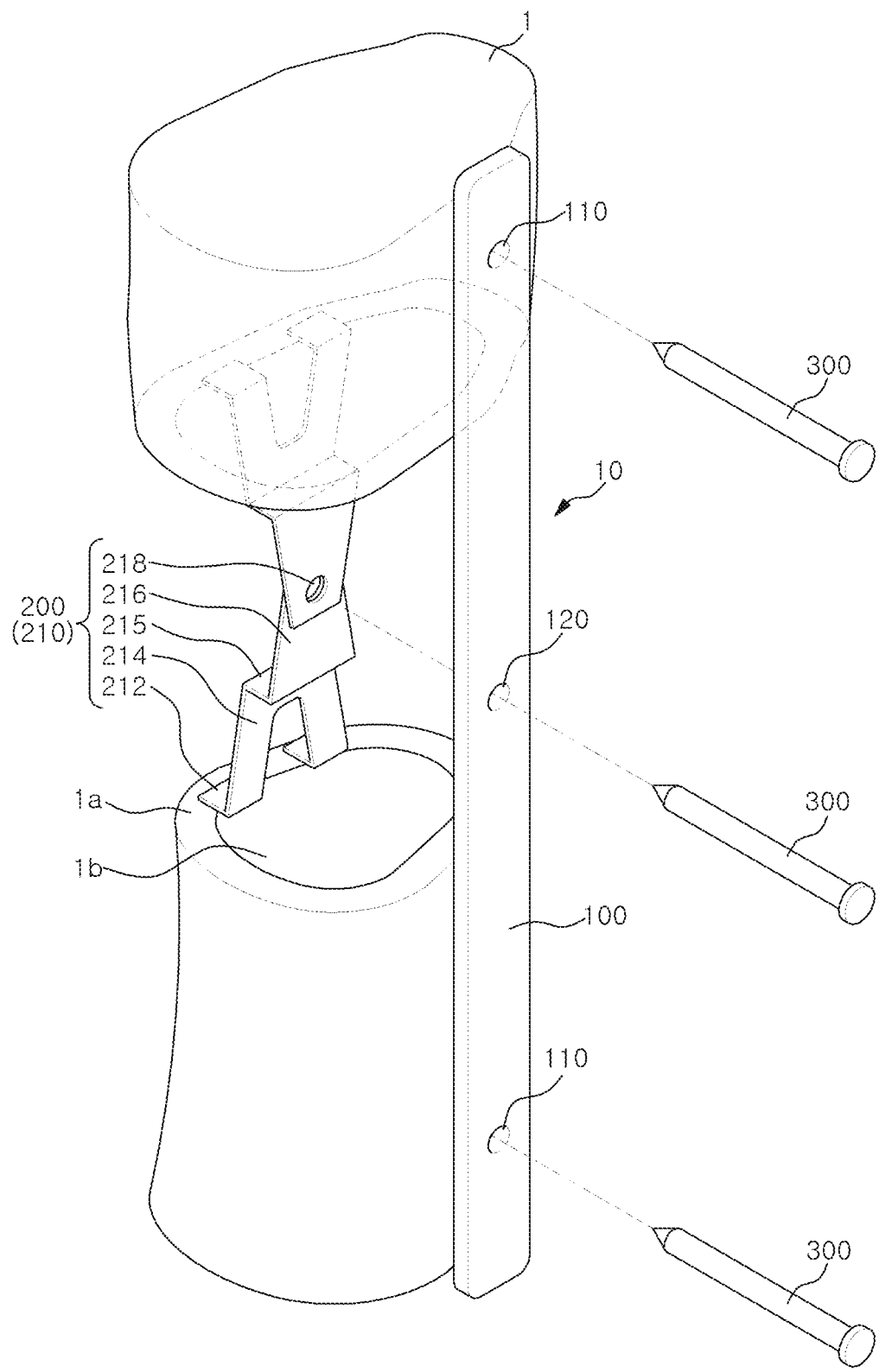
FIG. 3 is a view showing a scaffold for bone regeneration according to a modification of the embodiment of the present disclosure.

Meanwhile, the shape of the scaffold 10 according to the present embodiment may be variously modified. For example, as shown in FIG. 3, the support member 210 may have two or more contact portions 212, and the compact bone support portion 214 is formed to have the same number of branches as the number of the contact portions 212.

Figure 4:
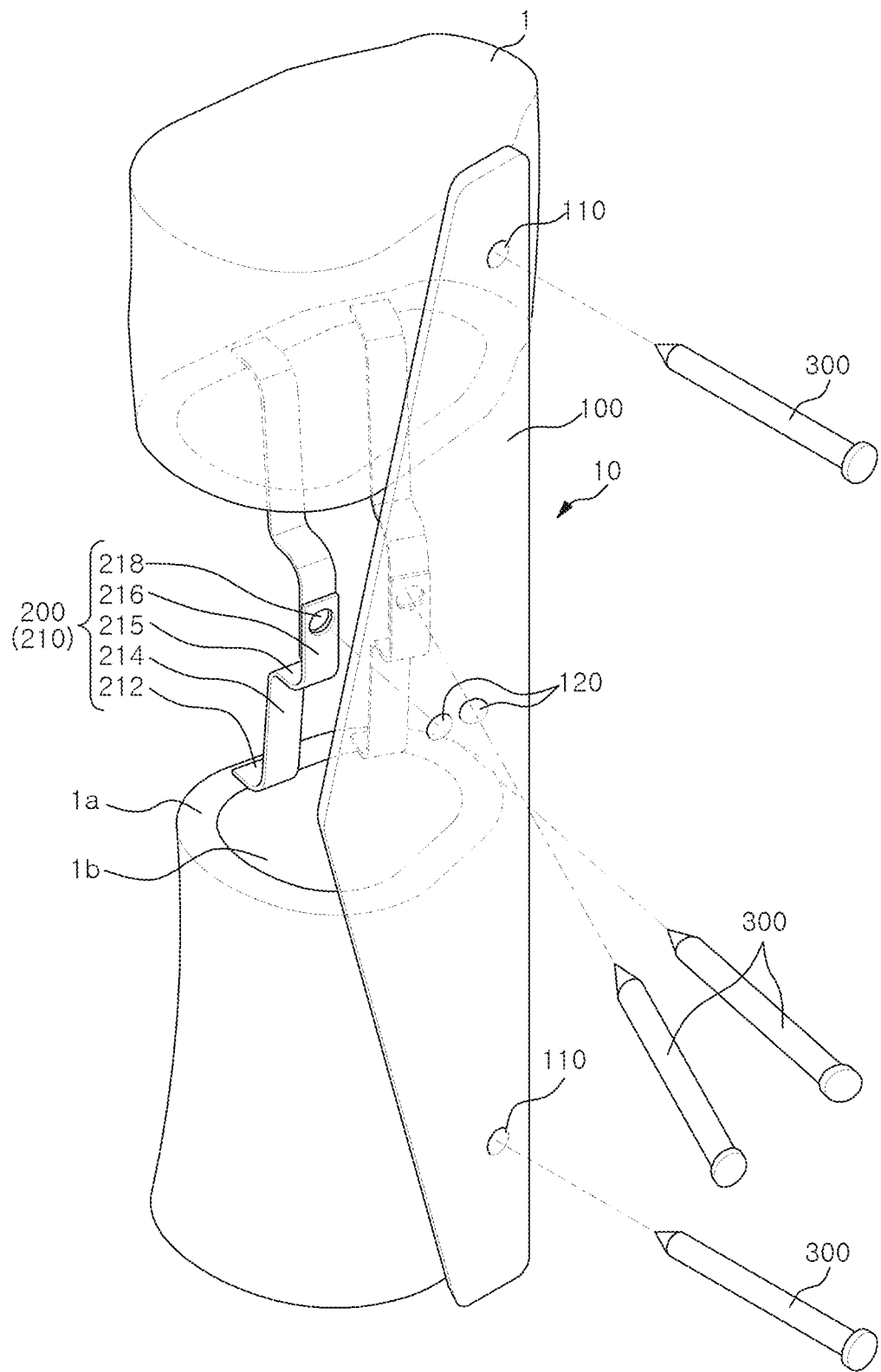
FIG. 4 is a view showing a scaffold for bone regeneration according to another modification of the embodiment of the present disclosure.

In addition, as shown in FIG. 4, the supporting pieces 210 are provided in a plurality of pairs, and the connecting holes 120 of the main support member 100 are also provided in plural, so that a plurality of fixing members 300 may be respectively inserted through the fastening holes 218 of the supporting pieces 210 and the corresponding connection holes 120 to fix the supporting pieces 210 to the the main support member 100.

Figure 5:
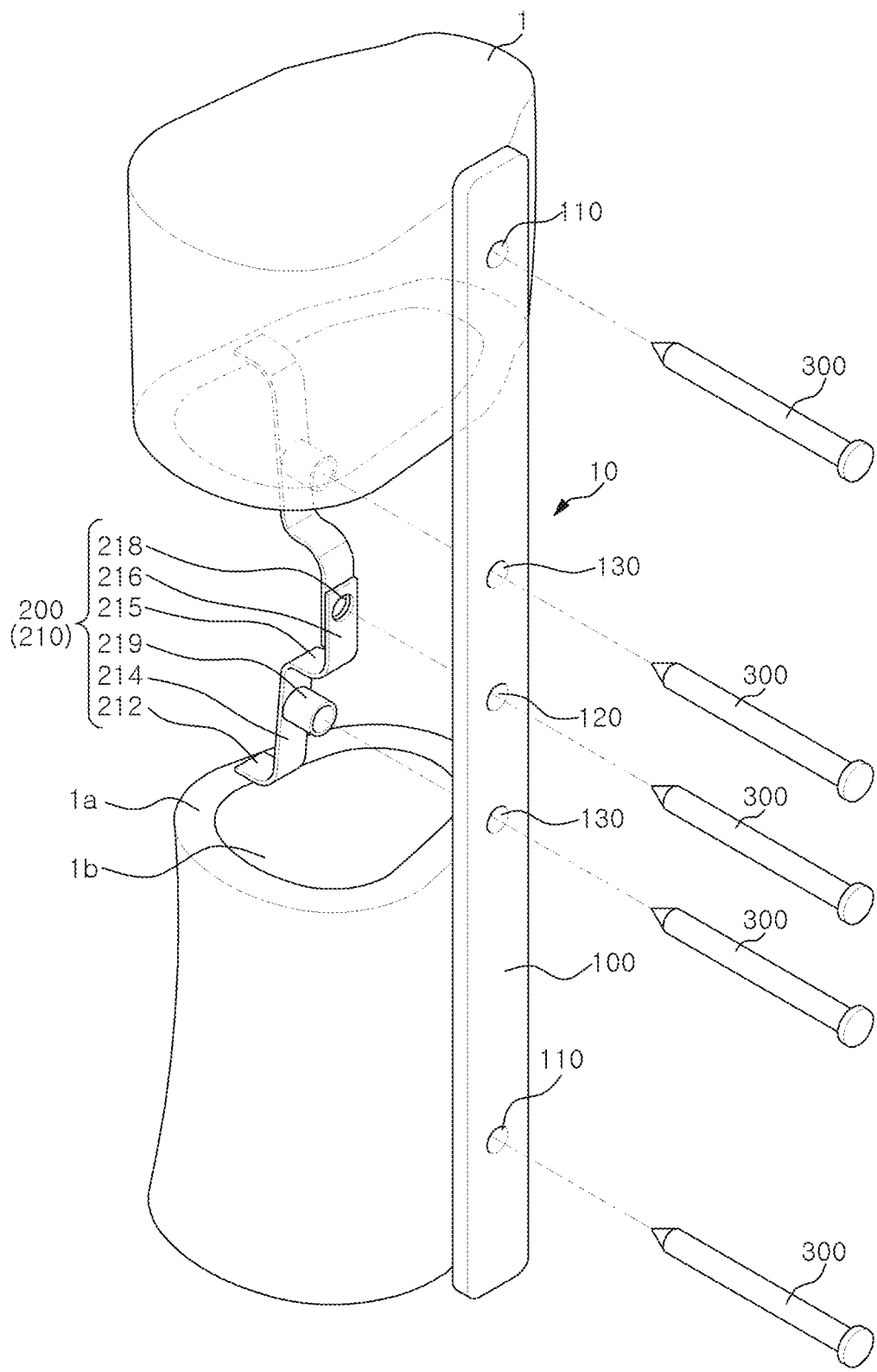
FIG. 5 is a view showing a scaffold for bone regeneration according to still another modification of the embodiment of the present disclosure.

Further, as shown in FIG. 5, an auxiliary hole 130 may be formed in the main support member 100 and the supporting piece 210 may further include a protruding portion 219 with a recess which protrudes from the compact bone support portion 214. The fixing member 300 is inserted through the auxiliary hole 130 into the recess of the protruding portion 219 so that the main support member 100 and the load supporting unit 200 can be coupled to each other.

Figure 10:
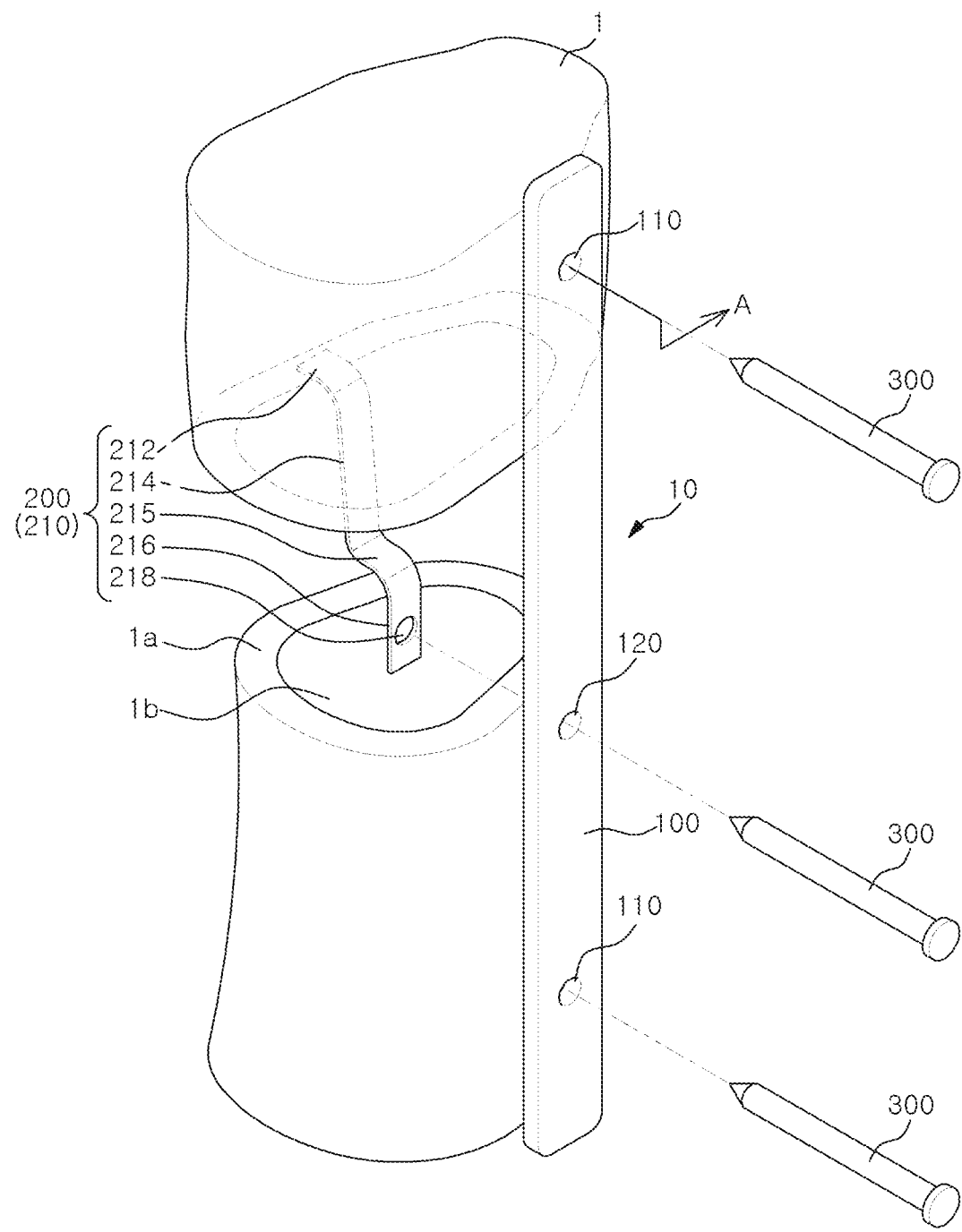
FIG. 10 is a view showing a scaffold for bone regeneration according to another embodiment of the present disclosure.

Alternatively, the load supporting unit 200 may include one supporting piece 210 as shown in FIG. 10. In this case, the contact portion 212 of the supporting member 210 is adapted to be brought in contact with and fixed to the compact bone 1a in the bone defect site of the bone 1. At this time, the contact portion 212 may be adhered to one of the opposite faces of the compact bone 1a or the side surface of the compact bone 1a.

The supporting piece 210 is selectively fixed to the main support member 100 by inserting the fixing member 300 through the connecting hole 120 of the main support member 100 into the fastening hole 218 formed in the load transfer interruption portion 216 of the supporting piece 210.

Hereinafter, a manufacturing system for manufacturing the scaffold 10 as described above and a method for manufacturing the scaffold 10 using the same will be described.

Figure 6:
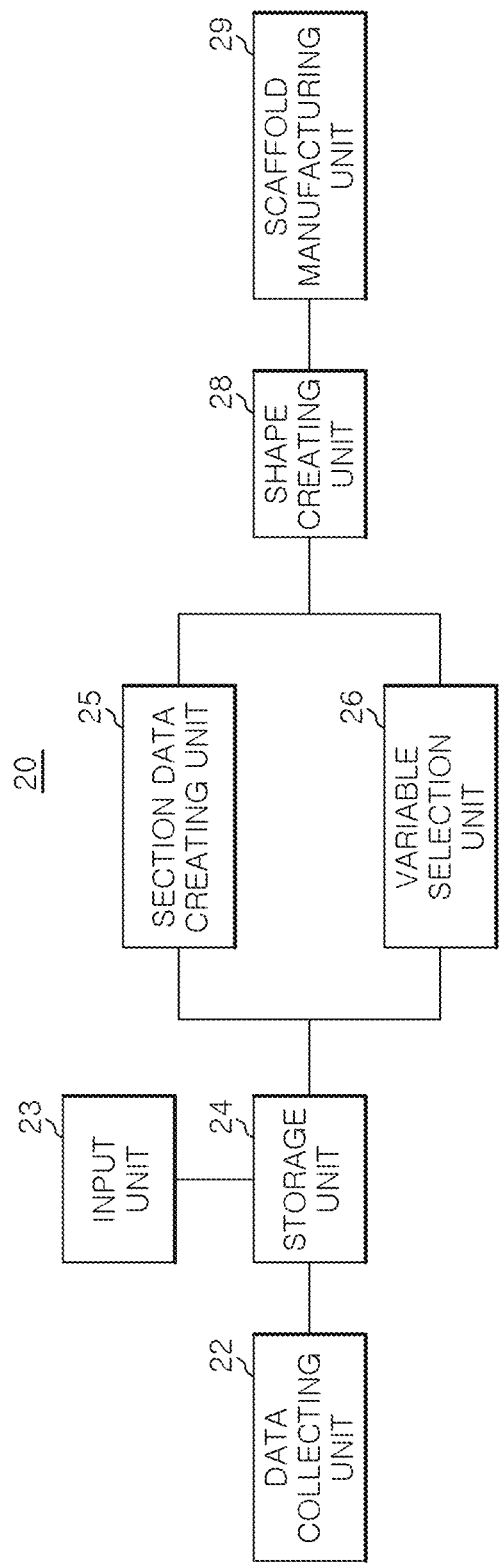
FIG. 6 is a block diagram illustrating a manufacturing system for manufacturing the scaffold shown in FIGS. 1 to 5.

Referring to FIG. 6, a scaffold manufacturing system 20 according to an embodiment of the present disclosure includes a data collecting unit 22, an input unit 23, a storage unit 24, a section data creating unit 25, a variable selection unit 26, a shape creating unit 28, and a scaffold manufacturing unit 29.

The data collecting unit 22 can acquire physical property data measured for each part of the human body and scan data of the bone defect site.

The physical property data measured for each part of the human body can be obtained by measuring loads, i.e., compression, tensile, bending, buckling and fatigue loads, applied to each body part according to daily movements for people with different heights and weights, using a test equipment which is separately provided. In addition, the data collecting unit 22 can acquire scan data obtained through a CT scan or the like for the bone defect site of a patient. The data collected by the data collecting unit 22 is transmitted to the storage unit 24 to be stored therein.

A user such as a doctor or the like can input required specifications and design constraints of the scaffold through the input unit 23. The required specifications and the design constraints may be, for example, the shape of a hole formed in a specific region, the distance between the respective members in a specific section, and the like. To this end, the input unit 23 may include an interface such as a keypad.

The required specifications and the design constraints inputted through the input unit 23 can be stored in the storage unit 24 and can be considered when the shape creating unit 28 creates section shape data of the scaffold.

The section data creating unit 25 obtains a regenerated image 3 of the bone defect site (see FIG. 8) using the scan data for the bone defect site obtained through the data collecting unit 22 and stored in the storage unit 24. The section data creating unit 25 creates section data for the bone defect site based on the obtained regenerated image 3. The sections of the regenerated image 3 may be indexed from $S_0$ to $S_n$.

The variable selection unit 26 can select design variables for the physical properties of the scaffold and the bone defect site.

At this time, the variable selection unit 26 can select the variables necessary for designing the scaffold by using the physical property data corresponding to the bone defect site among the physical property data for the human body stored in the storage unit 24 and the scan data for the bone defect site.

The design variables selected by the variable selection unit 26 includes at least one of a cross-sectional area, an allowable strength, a centroid, the moment of inertia with respect to the centroid, and principal axes of the moment of inertia.

The shape creating unit 28 creates the section shape data for the scaffold using the section data of the regenerated image 3, and generates data on the entire shape of the scaffold using the created section shape data.

At this time, the shape creating unit 28 may create the section shape data of the scaffold which corresponds to each section of the regenerated image 3.

The section shape data of the scaffold thus created can be matched one-to-one with the section data of the regenerated image 3 created by the section data creating section 25, and may be indexed from $S_0$ to $S_n$ like the section data of the regenerated image 3.

The shape creating unit 28 can creates section shape data by setting values of the design variables of the scaffold to fall within predetermined error ranges of the respective design variable values for the bone defect site selected by the variable selection unit 26.

Further, the shape creating unit 28 can create the section shape data of the scaffold while considering the required specifications and the design constraints inputted through the input unit 23.

In other words, the shape creating unit 28 can create the section shape data of the scaffold by considering not only the respective design variable values but also the inputted required specifications and the inputted design constraints.

The section shape data of the scaffold created by the shape creating unit 28 may be created in a single shape or may be created as a plurality of possible shapes satisfying the necessary conditions.

When the section shape data of the scaffold is created in a plurality of shapes, one of the possible shapes of the corresponding section may be selected by a user's input or may be arbitrarily selected.

In addition, the section shape data Si for any one section position among the section shape data of the scaffold created by the shape creating unit 28 may have a predetermined thickness, may have a constant thickness along the circumference, may have different thicknesses along the circumference, or may have a circumferentially discontinuous shape, which has a functional relationship with the properties of the compact bone of the bone defect site such as the shape and thickness of the compact bone.

The scaffold manufacturing unit 29 can produce a scaffold for bone regeneration based on the created overall shape data of the scaffold. The scaffold manufacturing unit 29 can produce a scaffold for bone regeneration by a method such as 3D printing, insert/injection molding, and the like.

Hereinafter, a method of manufacturing a scaffold using the manufacturing system 20 having the above-described configurations will be described.

Figure 7:
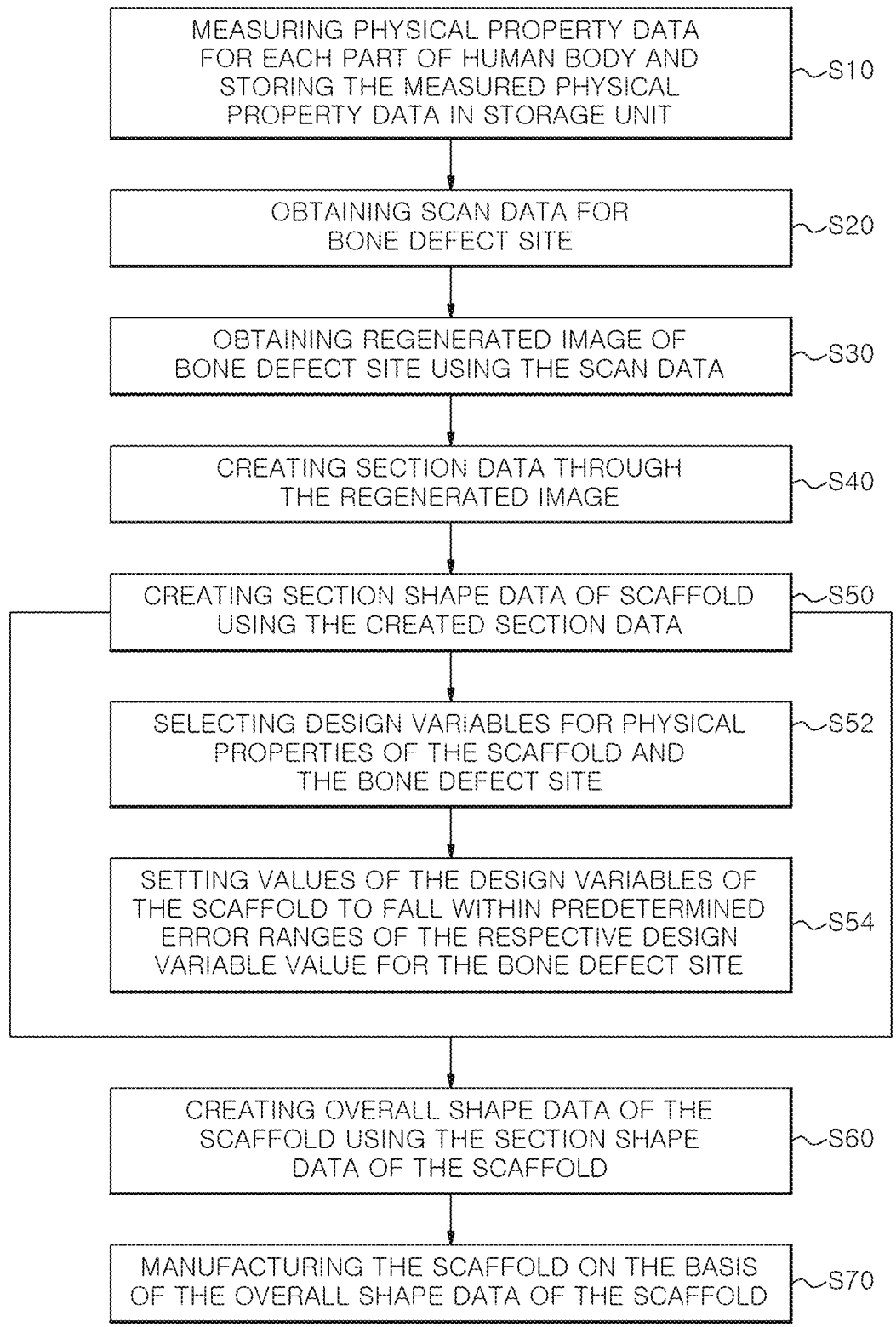
FIG. 7 is a flowchart showing a method for manufacturing a scaffold for bone regeneration using the manufacturing system shown in FIG. 6.

Referring to FIG. 7, a method of manufacturing a scaffold for bone regeneration according to an embodiment of the present disclosure includes step S10 of measuring physical property data for each part of a human body and storing the measured physical property data in the storage unit 24, step S20 of obtaining scan data for a bone defect site, step S30 of obtaining a regenerated image of the bone defect site using the scan data, step S40 of creating section data through the regenerated image, step S50 of creating section shape data of the scaffold using the section data, step S60 of creating the overall shape data of the scaffold using the section shape data of the scaffold, and step S70 of manufacturing the scaffold on the basis of the overall shape data of the scaffold.

In addition, the method of manufacturing a scaffold for bone regeneration according to the present embodiment may further include a step of receiving required specifications and design constraints of the scaffold through an input of a user such as a doctor or the like.

The required specifications and the design constraints may be, for example, the shape of a hole formed in a specific region, the distance between the respective members in a specific section, and the like.

The required specifications and the design constraints thus input may be stored in the storage unit 24 and may be considered when creating the section shape data of the scaffold in the step S50.

Figure 8:
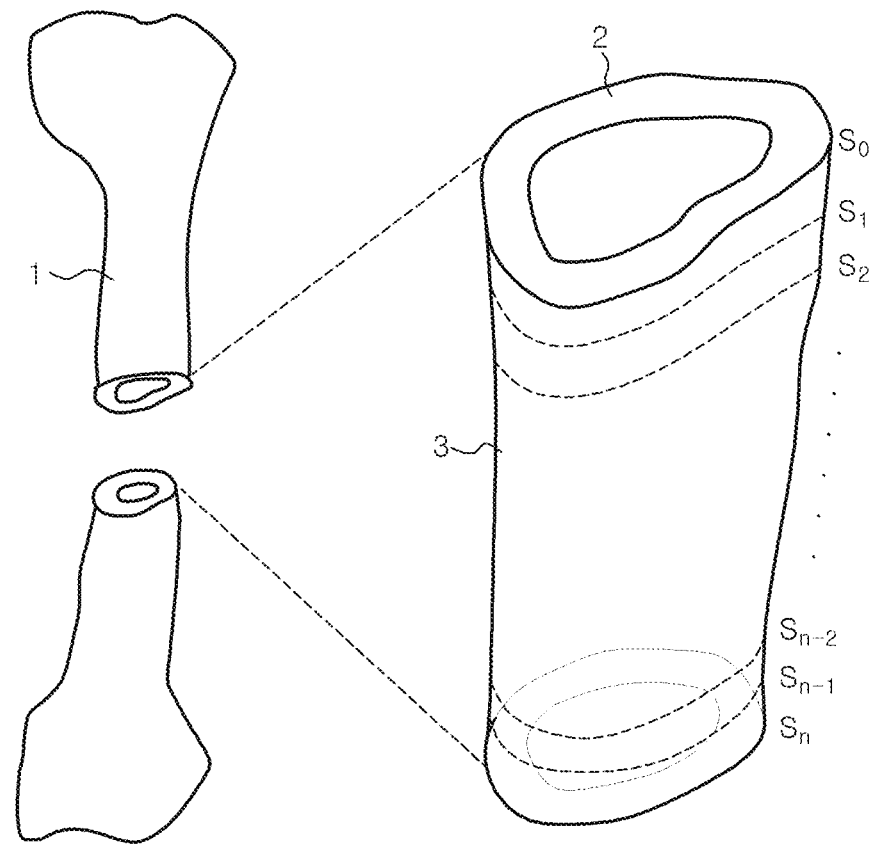
FIG. 8 is a conceptual diagram showing a process of obtaining a regenerated image using a scan image of a bone defect site in the manufacturing method shown in FIG. 7.
Figure 9:
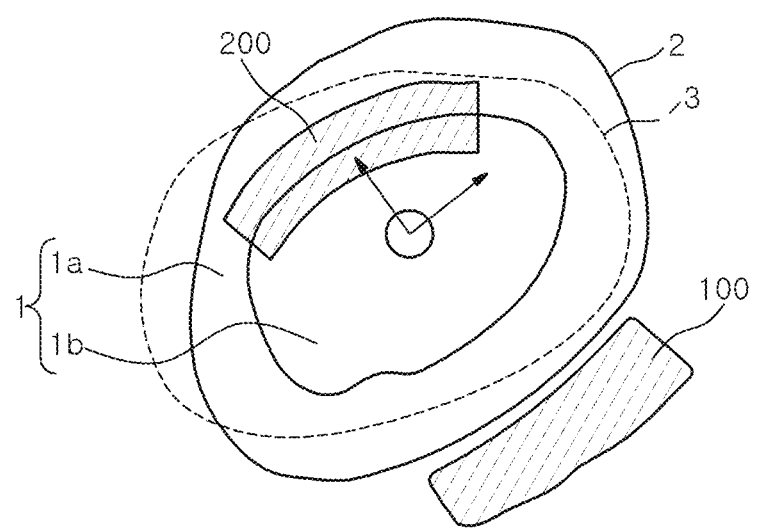
FIG. 9 shows a data image of the section shape of the scaffold in the manufacturing method of FIG. 7.

Referring to FIGS. 8 and 9, in the step S40 of creating section data through the regenerated image, section shape data obtained by cutting the regenerated image 3 of the bone defect site at predetermined intervals can be created. At this time, the sections of the regenerated image 3 may be indexed from $S_0$ to $S_n$.

Further, the step S50 of creating section shape data of the scaffold using the section data includes step S52 of selecting design variables for the physical properties of the scaffold and the bone defect site and step S54 of setting values of the design variables of the scaffold to fall within predetermined error ranges of the respective design variable values for the bone defect site.

At this time, the regenerated image 3 can be generated from the shape of the defect section 2 of the remaining bone 1 in the bone defect site by a pre-stored algorithm.

The first section shape of the scaffold is created to correspond to the outer shape of each section shape of the regenerated image 3 of the bone defect site as shown in FIG. 9, and then the final section shape of the scaffold can be created using the design variables selected by the variable selection unit 26.

The shapes of the scaffold according to the respective sections may be different from each other.

The section shape data of the scaffold may be created to be matched one-to-one with the section shapes of the regenerated image 3 from $S_0$ to $S_n$. Each section shape data of the scaffold may have a section shape having physical property similar to the physical property in accordance with each design variable value of the section shape data of the regenerated image 3 matched one-to-one with the section shape data of the scaffold.

In addition, the section shape data of the scaffold can be generated by considering the required specifications and the design constraints inputted through the input unit 23.

In other words, the section shape data of the scaffold can be created by considering not only the design variable values selected in the design variable selection step S52 but also the inputted required specifications and design constraints.

The section shape data of the scaffold may be generated in a single shape, or may be created in a plurality of possible shapes satisfying the necessary conditions. When the section shape data of the scaffold is created in a plurality of shapes, one of the possible shapes of the corresponding section may be selected by a user's input or may be arbitrarily selected.

In addition, the section shape data $S_i$ for any one section position among the section shape data of the scaffold created through the shape creating unit 28 may have a predetermined thickness, may have a constant thickness along the circumference, may have different thicknesses along the circumference, or may have a circumferentially discontinuous shape, which has a functional relationship with the properties of the compact bone of the bone defect site such as the shape and thickness of the compact bone.

Thus, the overall shape data of the scaffold can be created by smoothly connecting the final section shapes of the scaffold from $S_0$ to $S_n$.

According to the embodiments of the present disclosure, the rigidity of the scaffold is maintained during bone regeneration, and when the regenerated bone in the bone defect site has a sufficient rigidity after a certain period of time, a load can be applied to the regenerated bone even if the inserted scaffold is not removed.

While the embodiments of the present disclosure have been described with reference to the accompanying drawings, it will be understood by those skilled in the art that the present disclosure can be implemented in other specific forms without changing the technical spirit or essential features of the present disclosure. For example, those skilled in the art can implement the present disclosure in the form that is not clearly described in the embodiments of the present disclosure by changing materials, sizes and the like of the respective components depending on application fields or by combining or replacing the embodiments without departing from the scope of the present disclosure. Therefore, it should be noted that the above-described embodiments are merely illustrative in all aspects and are not to be construed as limiting the present disclosure and also that the modifications are included in the technical spirit of the present disclosure which is described in the following claims.

What is claimed is:

1. A scaffold for bone regeneration to be implanted at a bone defect site of a bone, the scaffold comprising:
   a main support member to be fixed to the bone; and
   a load supporting unit to be installed in the bone defect site of the bone to bear a load applied to the bone,
   wherein the load supporting unit includes a supporting piece having a shape bent in two or more steps, the supporting piece having a contact portion to be brought into contact with and fixed to a compact bone in the bone defect site of the bone,
   wherein the supporting piece includes:
   a compact bone support portion bent to extend from the contact portion, the compact bone support portion serving to bear a load applied to the compact bone, and
   wherein the main support member has an auxiliary hole formed therein,
   the supporting piece further includes a protruding portion protruding from the compact bone support portion, and
   the main support member and the load supporting unit are coupled to each other by a fixing member inserted through the auxiliary hole into a recess of the protruding portion.

2. The scaffold of claim 1, wherein the supporting piece further comprises:

a spongy bone support portion bent to extend from the compact bone support portion, the spongy bone support portion adapted to be disposed in a region overlapping a spongy bone of the bone in an extending direction of the bone; and a load transfer interruption portion bent to extend from the spongy bone support portion.

3. The scaffold of claim 2, wherein the supporting piece comprises two supporting pieces, and the supporting pieces are connected to each other by a fixing member inserted through fastening holes formed in the load transfer interruption portions of the supporting pieces.

4. The scaffold of claim 2, wherein the main support member includes a connecting hole formed therein, and a fixing member is inserted through the connecting hole and the fastening hole to fix the load transfer interruption portion to the main support member.

5. The scaffold of claim 3, wherein the main support member includes a connecting hole formed therein, and the fixing member is inserted through the connecting hole and the fastening holes to fix the load transfer interruption portions to the main support member.

6. The scaffold of claim 2, wherein the contact portion comprises a plurality of contact portions, and the compact bone support portion has the same number of branches as the number of the contact portions.

7. The scaffold of claim 3, wherein the contact portion comprises a plurality of contact portions, and the compact hone support portion has the same number of branches as the number of the contact portions.

8. A scaffold for bone regeneration to be implanted at a bone defect of a bone, the scaffold comprising:

a main support member to be fixed to the bone; and a load supporting unit to be installed in the bone defect site of the bone to selectively bear a load applied to the bone, wherein the load supporting unit includes two supporting pieces to be installed in the bone defect site of the bone to selectively bear the load applied to the bone, and the supporting pieces have at one end portions contact portions to be brought into contact with and fixed to opposite faces of a compact bone in the bone defect site of the bone, respectively, the other end portions of the supporting pieces being selectively coupled to or decoupled from each other, wherein each of the supporting pieces includes:

a first support portion extending from the contact portion in a direction away from corresponding one of the opposite faces of the compact bone, the first support portion serving to bear a load applied to the compact bone, and wherein the main support member has an auxiliary hole formed therein, each of the supporting pieces further includes a protruding portion protruding from the first support portion, and the main support member and the load supporting unit are coupled to each other by a fixing member inserted through the auxiliary hole into a recess of the protruding portion.

9. The scaffold of claim 8, wherein each of the supporting pieces further comprises:

a second support portion extending from the first support portion in a direction toward the main support member, the second support portion adapted to be disposed in a region overlapping a spongy bone in the bone defect site of the bone in an extending direction of the bone; and a third support portion extending from the second support portion in a direction away from the corresponding one of the opposite faces of the compact bone, wherein the supporting pieces are coupled to each other and fixed to the main support member by a fixing member inserted through a connecting hole formed in the main support member into fastening holes formed in the third support portions, and wherein the supporting pieces are decoupled from each other by removing the fixing member to interrupt a transfer of a load through the supporting pieces.

* * * * *